United States Patent
Kleen

(10) Patent No.: US 7,957,790 B2
(45) Date of Patent: *Jun. 7, 2011

(54) CATHETER

(75) Inventor: Martin Kleen, Neunkirchen (DE)

(73) Assignee: Siemens Aktiengesellschaft, Munich (DE)

( * ) Notice: Subject to any disclaimer, the term of this patent is extended or adjusted under 35 U.S.C. 154(b) by 365 days.

This patent is subject to a terminal disclaimer.

(21) Appl. No.: 11/040,431

(22) Filed: Jan. 21, 2005

(65) Prior Publication Data

US 2005/0187467 A1    Aug. 25, 2005

(30) Foreign Application Priority Data

Jan. 21, 2004   (DE) .................. 10 2004 003 166

(51) Int. Cl.
*A61B 6/00* (2006.01)

(52) U.S. Cl. .................................................... 600/433

(58) Field of Classification Search .... 604/95.01–95.05, 604/528, 101.01, 101.05; 600/433
See application file for complete search history.

(56) References Cited

U.S. PATENT DOCUMENTS

| | | | | |
|---|---|---|---|---|
| 2,855,934 A * | 10/1958 | Daughaday, Jr. | .......... | 604/95.03 |
| 3,773,034 A * | 11/1973 | Burns et al. | .................... | 600/434 |
| 4,176,662 A * | 12/1979 | Frazer | .......................... | 600/114 |
| 4,292,961 A * | 10/1981 | Kawashima | ................. | 600/145 |
| 4,406,656 A * | 9/1983 | Hattler et al. | ................. | 604/523 |
| 4,543,090 A * | 9/1985 | McCoy | ....................... | 604/95.05 |
| 4,681,122 A * | 7/1987 | Winters et al. | ................ | 600/549 |
| 4,690,131 A * | 9/1987 | Lyddy et al. | ................... | 600/115 |
| 4,799,474 A * | 1/1989 | Ueda | .............................. | 600/151 |
| 4,813,434 A | 3/1989 | Buchbinder et al. | | |
| 4,838,859 A * | 6/1989 | Strassmann | ................ | 604/95.03 |
| 4,878,495 A * | 11/1989 | Grayzel | ........................ | 606/193 |
| 4,884,557 A * | 12/1989 | Takehana et al. | ............. | 600/145 |
| 4,904,048 A * | 2/1990 | Sogawa et al. | ................ | 385/118 |
| 4,930,494 A * | 6/1990 | Takehana et al. | ............. | 600/145 |
| 4,983,165 A | 1/1991 | Loiterman | | |
| 5,090,259 A * | 2/1992 | Shishido et al. | ............. | 73/866.5 |
| 5,123,421 A * | 6/1992 | Sinofsky | ........................ | 600/585 |
| 5,154,179 A * | 10/1992 | Ratner | .......................... | 600/420 |
| 5,235,964 A * | 8/1993 | Abenaim | ........................ | 600/139 |
| 5,300,048 A * | 4/1994 | Drewes et al. | ................. | 604/529 |
| 5,308,323 A * | 5/1994 | Sogawa et al. | ............. | 604/95.03 |
| 5,322,064 A * | 6/1994 | Lundquist | ..................... | 600/381 |

(Continued)

FOREIGN PATENT DOCUMENTS

WO      0013733 A2    3/2000

(Continued)

OTHER PUBLICATIONS

Mark A Saab, "Applications of High-Pressure Balloons in the Medical Device Industry", 1999, pp. 1-19, Advanced Polymers, Inc., retrieved from Internet Jun. 11, 2010 htt://www.advpoly.com/Documents/MedicalBalloonPaper.pdf.

(Continued)

*Primary Examiner* — Kevin C Sirmons
*Assistant Examiner* — Michael J Anderson

(57) ABSTRACT

Catheter for inserting into a hollow organ, in particular a blood vessel, wherein at least one tube- or balloon-like flexural element (12, 12a, . . . , 12l) which can be filled with a filling medium is provided inside the catheter, which flexural element is flexible in the non-pressurized state and stiffens as a result of pressure buildup internally and assumes a predetermined curved shape.

18 Claims, 3 Drawing Sheets

U.S. PATENT DOCUMENTS

| | | | | |
|---|---|---|---|---|
| 5,391,147 A | * | 2/1995 | Imran et al. | 604/528 |
| 5,415,633 A | * | 5/1995 | Lazarus et al. | 604/95.05 |
| 5,458,574 A | * | 10/1995 | Machold et al. | 604/101.03 |
| 5,487,757 A | * | 1/1996 | Truckai et al. | 604/264 |
| 5,573,007 A | * | 11/1996 | Bobo, Sr. | 600/561 |
| 5,603,697 A | * | 2/1997 | Grundy et al. | 604/95.04 |
| 5,624,380 A | * | 4/1997 | Takayama et al. | 600/146 |
| 5,645,529 A | * | 7/1997 | Fagan et al. | 604/101.01 |
| 5,662,587 A | * | 9/1997 | Grundfest et al. | 600/114 |
| 5,810,717 A | * | 9/1998 | Maeda et al. | 600/151 |
| 5,865,801 A | * | 2/1999 | Houser | 604/103.07 |
| 5,899,882 A | * | 5/1999 | Waksman et al. | 604/103.07 |
| 5,908,446 A | * | 6/1999 | Imran | 607/122 |
| 5,916,147 A | * | 6/1999 | Boury | 600/146 |
| 5,971,983 A | * | 10/1999 | Lesh | 606/41 |
| 6,036,636 A | * | 3/2000 | Motoki et al. | 600/146 |
| 6,071,281 A | * | 6/2000 | Burnside et al. | 606/41 |
| 6,142,994 A | * | 11/2000 | Swanson et al. | 606/41 |
| 6,146,339 A | * | 11/2000 | Biagtan et al. | 600/585 |
| 6,162,171 A | * | 12/2000 | Ng et al. | 600/141 |
| 6,319,244 B2 | * | 11/2001 | Suresh et al. | 604/525 |
| 6,425,895 B1 | * | 7/2002 | Swanson et al. | 606/41 |
| 6,468,203 B2 | * | 10/2002 | Belson | 600/146 |
| 6,595,914 B2 | * | 7/2003 | Kato | 600/152 |
| 6,610,007 B2 | * | 8/2003 | Belson et al. | 600/146 |
| 6,645,200 B1 | * | 11/2003 | Koblish et al. | 606/41 |
| 6,679,836 B2 | * | 1/2004 | Couvillon, Jr. | 600/146 |
| 6,699,179 B2 | * | 3/2004 | Wendlandt | 600/114 |
| 6,764,441 B2 | * | 7/2004 | Chiel et al. | 600/115 |
| 6,770,027 B2 | * | 8/2004 | Banik et al. | 600/146 |
| 6,800,056 B2 | * | 10/2004 | Tartaglia et al. | 600/114 |
| 6,837,846 B2 | * | 1/2005 | Jaffe et al. | 600/114 |
| 6,858,005 B2 | * | 2/2005 | Ohline et al. | 600/141 |
| 6,869,396 B2 | * | 3/2005 | Belson | 600/146 |
| 6,875,170 B2 | * | 4/2005 | Francois et al. | 600/141 |
| 6,890,297 B2 | * | 5/2005 | Belson | 600/145 |
| 6,923,768 B2 | * | 8/2005 | Camus et al. | 600/463 |
| 6,936,015 B2 | * | 8/2005 | Esashi et al. | 600/585 |
| 6,939,338 B2 | * | 9/2005 | Waldhauser et al. | 604/531 |
| 6,974,411 B2 | * | 12/2005 | Belson | 600/114 |
| 6,984,203 B2 | * | 1/2006 | Tartaglia et al. | 600/114 |
| 6,997,870 B2 | * | 2/2006 | Couvillon, Jr. | 600/146 |
| 6,997,941 B2 | * | 2/2006 | Sharkey et al. | 607/96 |
| 7,044,907 B2 | * | 5/2006 | Belson | 600/146 |
| 7,063,682 B1 | * | 6/2006 | Whayne et al. | 604/95.04 |
| 7,087,013 B2 | * | 8/2006 | Belson et al. | 600/145 |
| 7,097,615 B2 | * | 8/2006 | Banik et al. | 600/146 |
| 7,101,362 B2 | * | 9/2006 | Vanney | 604/523 |
| 7,128,956 B2 | * | 10/2006 | Wang et al. | 428/36.9 |
| 7,211,082 B2 | * | 5/2007 | Hall et al. | 606/41 |
| 2001/0044591 A1 | * | 11/2001 | Stevens et al. | 604/6.11 |
| 2002/0177765 A1 | * | 11/2002 | Bowe et al. | 600/374 |
| 2003/0004460 A1 | * | 1/2003 | Bedell | 604/95.04 |
| 2003/0100824 A1 | * | 5/2003 | Warren et al. | 600/407 |
| 2003/0149338 A1 | | 8/2003 | Francois et al. | |
| 2003/0171736 A1 | * | 9/2003 | Bon | 604/525 |
| 2003/0199818 A1 | * | 10/2003 | Waldhauser et al. | 604/95.05 |
| 2003/0212395 A1 | * | 11/2003 | Woloszko et al. | 606/41 |
| 2003/0216721 A1 | * | 11/2003 | Diederich et al. | 606/28 |
| 2004/0116957 A1 | * | 6/2004 | Nishide et al. | 606/194 |
| 2004/0147837 A1 | * | 7/2004 | Macaulay et al. | 600/424 |
| 2005/0148836 A1 | * | 7/2005 | Kleen et al. | 600/374 |
| 2005/0165366 A1 | * | 7/2005 | Brustad et al. | 604/264 |
| 2005/0187467 A1 | * | 8/2005 | Kleen | 600/433 |
| 2005/0203371 A1 | * | 9/2005 | Kleen | 600/407 |
| 2005/0228274 A1 | * | 10/2005 | Boese et al. | 600/433 |
| 2005/0228290 A1 | * | 10/2005 | Borovsky et al. | 600/466 |
| 2006/0084964 A1 | * | 4/2006 | Knudson et al. | 606/41 |
| 2006/0135961 A1 | * | 6/2006 | Rosenman et al. | 606/108 |
| 2006/0142695 A1 | * | 6/2006 | Knudson | 604/95.04 |
| 2006/0189928 A1 | * | 8/2006 | Camus et al. | 604/101.01 |

FOREIGN PATENT DOCUMENTS

| WO | 0076570 A2 | 12/2000 |
|---|---|---|

OTHER PUBLICATIONS

"API Expands Pet Heat Shrink Tubing Line Again with Smallest Sizes Ever; Offers Broadest Range of Small Diameter Tubing Industry", 2002, Advanced Polymers Inc. Press Release; http://www.devicelink.com/press_release/mdl/advpoly.html.

Wikipedia—article on "Catheter", Sep. 6, 2007, http://en.wikipedia.org/wiki/Catheter.

* cited by examiner

CATHETER

CROSS REFERENCE TO RELATED APPLICATIONS

This application claims priority to the German application No. 10 2004 003 166.5, filed Jan. 21, 2004 which is incorporated by reference herein in its entirety.

FIELD OF INVENTION

The invention relates to a catheter for inserting into a hollow organ, in particular a blood vessel.

BACKGROUND OF INVENTION

Flexible catheters which are advanced through arteries or veins are used for intravascular or intracardial treatment. At the tip or side of said catheters functional mechanisms are provided, for example to stimulate or cauterize tissue or to conduct electrical signals. In order to be able to deliver the catheter to the correct positions in the cardiac or vascular system, the catheters have to be moved and guided by the physician. Such guidance has to be precise, fast and highly flexible, in particular because the vascular system is a convoluted system that contains a number of bends. Most of the time during treatment is taken up by the navigation of the catheter. Catheters of this kind are conventionally steered solely by manipulating the end that projects out of the patient. By rotating, pushing forward and retracting the catheter, said actions being observed through X-ray monitoring, in combination with a curvature in the tip of the catheter, the catheter tip is caused to take the desired route, which the rest of the catheter then follows. A catheter of this kind moved by the user has to be relatively stiff so that movements can be reliably continued also when negotiating bends. This runs counter to safety requirements, however, since a stiff catheter is more likely to cause injuries.

SUMMARY OF INVENTION

A known guidance method is the use of pull wires that allow the end of the catheter to be moved. The disadvantage thereof is firstly the complexity of the catheter and secondly the limited angle of curvature that can be set. A further known technique is magnetic navigation. This type of catheter has at its end, which is designed to be extremely flexible, a tip comprising magnetic material. By applying an external homogeneous magnetic field through the patient it is possible for the catheter tip and thus the whole of the end of the catheter to be aligned along the lines of the magnetic field. By also advancing the catheter it is possible to navigate through complex vascular systems. However, the above method requires a substantial outlay in terms of technology, equipment and cost, and furthermore the size of the area that can be navigated is limited due to the dimensions of the magnetic field.

The invention addresses the problem of providing a catheter that allows simple navigation.

To solve the above problem there is provided according to the invention a catheter of the type cited at the beginning, inside of which there is provided at least one tube- or balloon-like flexural element which can be filled with a filling medium, which is flexible in a non-pressurized state and which stiffens due to the buildup of pressure inside it and assumes a predetermined curved shape.

Using the flexural element usefully provided on the catheter tip side, a curvature of the catheter can be achieved in a simple manner when required. Said curvature allows the catheter to adapt to the subsequent course of the blood vessel and to be threaded in a simple manner into a branch of a blood vessel, for example. For this purpose, the flexural element, which is flexible in a non-pressurized state, has simply to be filled with the filling medium in order to build up the pressure. As a result of the increasing pressure the flexural element increasingly stiffens and assumes a predetermined curved shape. According to the filling level, any intermediate shape ranging from completely flexible to completely stiff can be set, there being various degrees of rigidity. Depending on the embodiment of the flexural element, any desired angles of curvature can therefore be set in the stiffened state.

It is useful if a plurality of individually controllable flexural elements are provided so that, according to the position of the catheter and the required curvature, a required flexural element can be activated and the catheter or, as the case may be, the catheter tip, which in this catheter is sufficiently flexible and so designed to avoid a risk of injury when the catheter is advanced, can flex in the right direction.

In this case the flexural elements can be arranged in such a way that the predetermined directions of deformation are aligned to different directions. The multiple flexural elements thus all curve in a different direction, with the result that a high degree of flexibility is achieved with respect to the catheter tip deformation. According to a first invention alternative the flexural elements can be arranged sequentially essentially in the center of the catheter relative to the longitudinal axis of the catheter. In other words the flexural elements, which are dimensioned to be relatively short in this case, are arranged one after the other in series. Furthermore it is also possible that at least some of the flexural elements are disposed in a distributed arrangement about the longitudinal axis of the catheter. In this case, therefore, the flexural elements are staggered radially outward; they are disposed in a distributed arrangement around the internal catheter cavity in which, for example, signal lines or similar are run. In this way a fully variable tip deformation can be set in particular for different preferred directions of flexure.

A development of the inventive idea provides that a plurality of flexural elements are arranged at a common longitudinal position relative to the longitudinal axis of the catheter, that is to say that relative to the length of the catheter they are disposed staggered radially outward at one point or in a segment-like arrangement at a plurality of points. Alternatively it is possible to dispose said elements in a distributed arrangement over a part of the length of the catheter, in other words to provide any number of flexural elements over a specific length of the catheter in a distributed and staggered arrangement with respect to one another in order to achieve an adequate flexural capability relative to said longitudinal section at a plurality of different locations. The length along which the flexural elements are disposed in the aforementioned arrangements can be selected at random and usually depends on the purpose for which the catheter is used and the possibility of integrating the flexural elements.

A flexural element itself is usefully made from a non-elastic material. In order to achieve the defined shape in the filled state, the walls thereof are non-symmetrical in design, that is to say the lengths of the side walls are different, with the result that a curved shape is produced in the filled state. Usefully, polyurethane or polytetrafluoroethylene is utilized for this purpose, in other words materials that are non-elastic, thereby avoiding any stretching of the material that would result in an approximation to a spherical shape.

A fluid can be used as the filling medium; possible fluids include, for example, water or a saline solution or another, preferably biocompatible, fluid. Alternatively, a gaseous filling medium such as air or oxygen or also a different, preferably biocompatible, gas can be used.

Since, as described above, the simple means of navigation is based on the situation-dependent activation of the flexural element or elements, a development of the inventive idea for simple and fast setup of the catheter, in other words when it is needed and is to be used, provides that it has a central connection device for a feed device for the filling medium, at which connection device the or all lines for the filling medium leading to the flexural element or elements converge. Thus, a defined connection point for all fluid or gas feed lines is provided, usefully in the form of a simple plug-in connection to which a corresponding counterpart can be connected as part of a feed device.

All in all, the catheter according to the invention allows easy navigation without a large outlay in terms of external equipment. All that is required is a feed device which simultaneously handles control functions in order to activate the flexural elements. In particular with a distribution of a plurality of flexural elements over a specific length of the catheter, control of the catheter curvature is also advantageously possible not only at the end of the catheter, but quasi segmentally or approximately randomly at different points of the catheter. It is also conceivable to be able to vary the flexibility or stiffness of the catheter over the entire length along which the flexural elements are distributed, or only over a part thereof. For it is of course possible to put a plurality of flexural elements, of a segment for example, under pressure simultaneously so that their forces cancel one another out and the catheter does not deform but stiffens in sections. It is therefore possible to stiffen the catheter over the entire length along which the flexural elements are distributed, or only over a section thereof. In this way it is possible to minimize the risk of injury, where this is necessary because of the anatomical conditions, as well as to optimize the controllability and "pushability", where this is possible from the point of view of risk of injury. The controllable curvature at any point of the catheter over the range of the flexural elements also results in the curvatures along the vascular structures exerting no deformation force from the catheter on the vascular walls, since of course there is also the possibility of producing corresponding vascular curvatures on the catheter side, even if the catheter tip has already long since passed this section. The shape of the catheter thus adapts itself as far as possible to the actual shape of the blood vessel, and the vascular walls are not too greatly irritated and deformed via the catheter. This reduces the risk of injury during interventions.

In addition to the catheter the invention also relates to a catheter device, comprising a catheter of the above-described kind, as well as a feed device for the filling medium which can be coupled to the catheter. This is usefully embodied for separate activation of the plurality of flexural elements provided on the catheter side. In order to perform a precise activation, the feed device must know the assignment of the individual feed lines to the respective flexural element and of course the latter's position on the catheter side. For this purpose means for identifying the feed lines converging at the connection device on the catheter side are usefully provided at the catheter and/or the feed device. Said identifying means can be a type of plug-in coding, for example, or any other signaling means which allows a unique assignment of the respective line to the flexural element. For only then can it be guaranteed that the feed device activates the right flexural element for the desired curvature locally and with regard to the direction of curvature.

The feed device itself can be embodied for automatic activation of the required flexural element or elements as a function of at least one item of information relating to the desired direction of curvature of the catheter. Said information can be provided for example by the physician who is continuing, as before, to control the movement of the catheter with the aid of X-ray monitoring. If he or she sees that the tip must be curved in one direction or the other, he/she can supply this information to the feed device, which subsequently performs the automatic activation. For this purpose an input device for this information can usefully be provided, which input device, according to a particularly advantageous embodiment of the invention, comprises a monitor on which it is possible to display a three-dimensional image of the blood vessel and the catheter, in which displayed image the user can define the direction of curvature by means of a marker or suchlike, for example a cursor. In other words, the physician is presented with a preferably three-dimensional display of a blood vessel tree along with the catheter, which display can be produced in any manner, via parallel X-ray monitoring or using other sets of image data that were obtained from previous investigations (for example magnetic resonance tomography or computer tomography) and which incorporate the catheter image as captured via the X-ray monitoring. The physician now has the ability to navigate in the displayed image, for example via the monitor cursor, and to define a desired direction of curvature. According to the information supplied, the feed device is then able to perform the corresponding activation in order to achieve the desired curvature.

BRIEF DESCRIPTION OF THE DRAWINGS

Further advantages, features and details of the invention will become apparent from the exemplary embodiments described below and by reference to the drawings, in which.

DETAILED DESCRIPTION OF INVENTION

Figure 1:
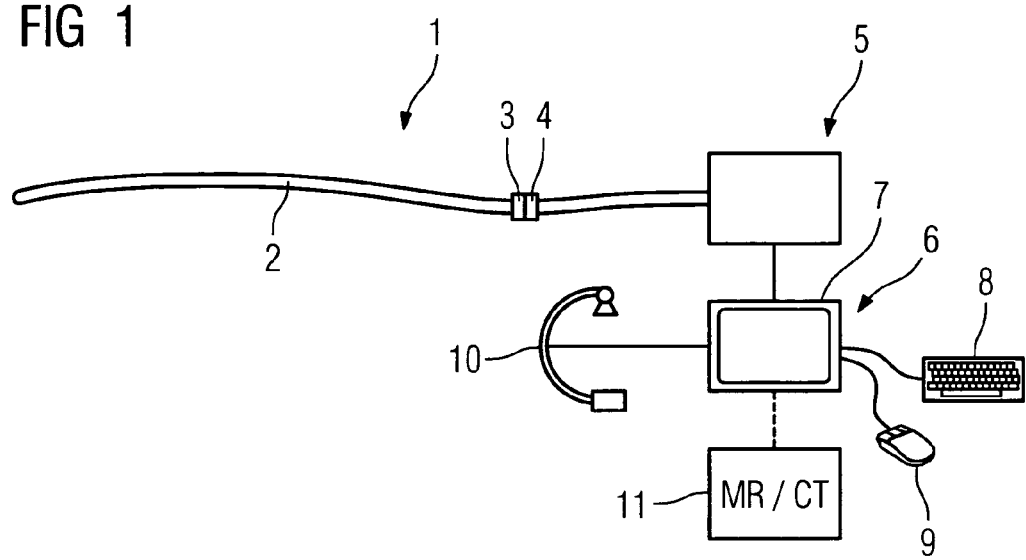
FIG. 1 shows a schematic diagram illustrating the principle of a catheter device according to the invention.

FIG. 1 shows a catheter device 1 according to the invention comprising a catheter 2, at the free end of which (i.e. the end that is not to be inserted into the patient) there is provided a connection device 3 which is coupled to a connection device 4 that forms part of a feed device 5 for a liquid or gaseous filling medium. By means of said feed device 5, a liquid or gaseous filling medium can be supplied to the individual flexural elements which are integrated into the catheter and which are hereinafter described in further detail. The feed device 5 is coupled to an input device 6 comprising a monitor 7, a keyboard 8 and a mouse 9. By means of said device, the operator, referring to an image displayed on the monitor 7, said image being supplied for example by an X-ray image taken in parallel by an X-ray device 10 during the invasive procedure, or where appropriate using an image data set 11, obtained for example by magnetic resonance tomography or computer tomography, can specify the direction in which the catheter is to be bent.

Figure 2:
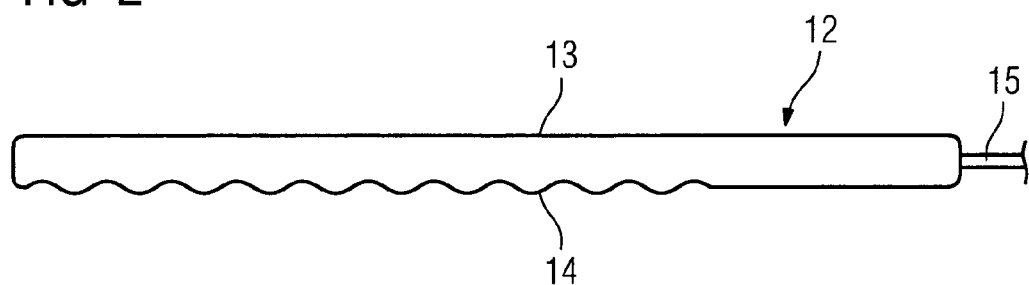
FIG. 2 shows a schematic diagram depicting a flexural element in the non-pressurized state.
Figure 3:
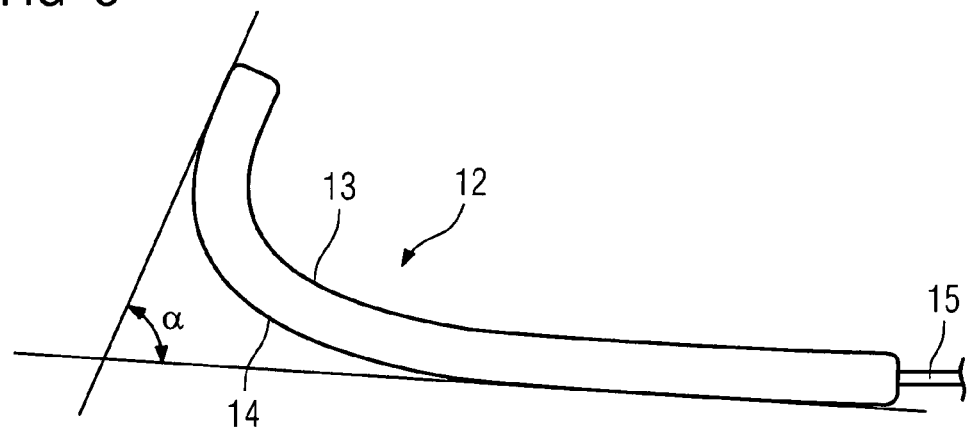
FIG. 3 shows a schematic diagram of the flexural element from FIG. 2 in the filled state.
Figure 4:
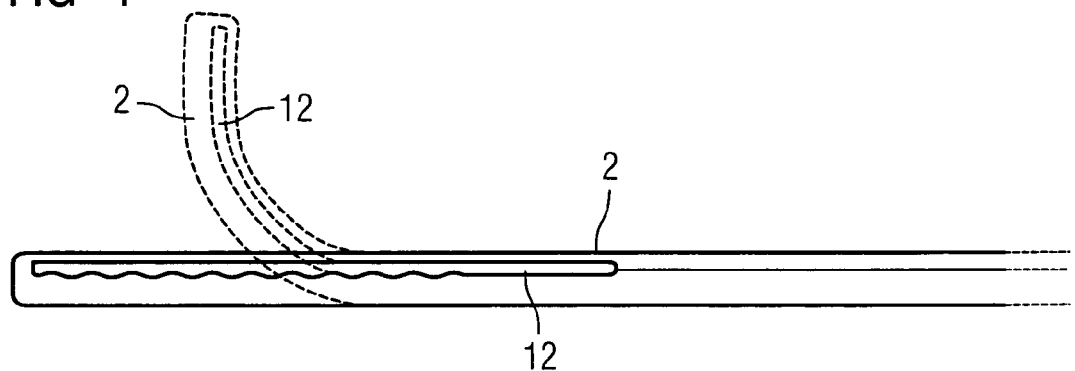
FIG. 4 shows a schematic diagram of the catheter tip with non-pressurized flexural element and filled flexural element.

The functional principle is based on the fact that there are integrated in the catheter one flexural element or a plurality of flexural elements which, when pressure builds up inside the catheter, can be directed into a particular shape. FIG. 2 shows a schematic diagram illustrating a flexural element 12 which is tube-like in design. Said element consists of a non-elastic plastic material, for example PUR or PTFE, but any other plastic can be used. The flexural element 12 has a shorter wall segment 13 on one side, while a longer wall segment 14 is provided on the opposite side; in other words, the walls are non-symmetrical overall. If filling medium, for example water, saline solution or air or oxygen, is now supplied via the feed line 15, then the pressure builds up inside, resulting in the flexural element 12 attempting to achieve a maximum volume in a minimum surface area. Since the walls are non-elastic, no stretching can occur. The wall 14 stretches such that the flexural element 12 assumes the curved shape shown in FIG. 3, in which it is sufficiently stiff as a result of the pressure inside the catheter. The diagram shows how a curvature that is created by the geometrical shape of the flexural element 12 can be set in this way. In the example shown, the angle of curvature α is drawn. If such a flexural element is now integrated into the catheter 2, as shown schematically in FIG. 4, a defined deformation of the catheter can be achieved. In the non-pressurized state the flexural element 12 is flexible, that is to say it has not been stiffened and the shape thereof is determined by the shape of the catheter or catheter sheath. The catheter sheath consists, for example, of a slightly elastic plastic material and possesses sufficient stiffness or rigidity to allow manipulation of the catheter. As the diagram shows, the shape of the catheter 2 changes when the flexural element 12 is subjected to pressure, as indicated by the dashed lines in FIG. 4. As shown in FIG. 4, the catheter curves upward, essentially describing a curvature of 90°, caused by the defined alteration in shape of the flexural element 12. If pressure on the flexural element 12 is released again, said element becomes flexible again and collapses, as it were, possibly with the assistance of the resetting force of the slightly elastic catheter sheath.

Figure 5:
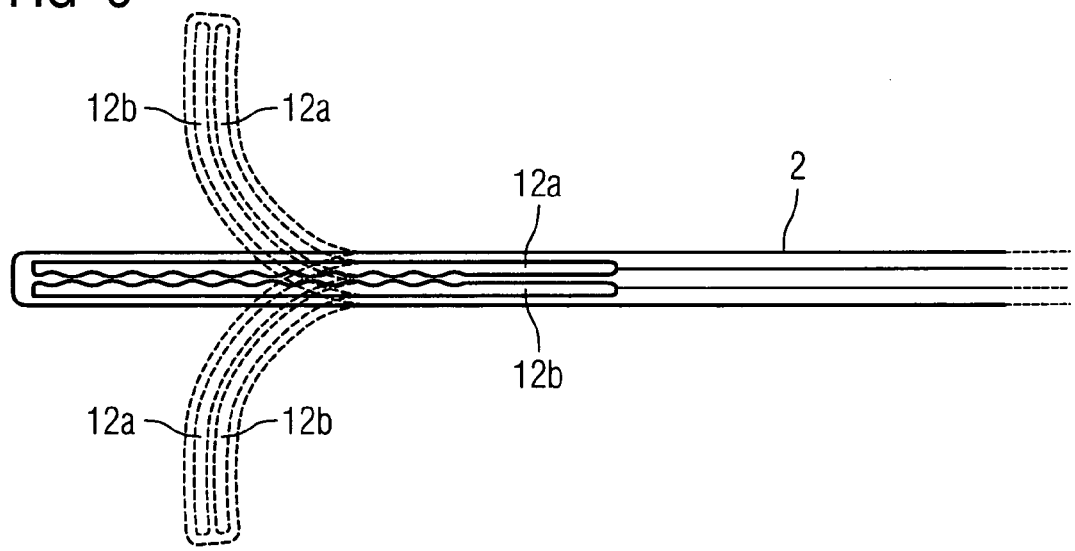
FIG. 5 shows a schematic diagram of the catheter tip having two flexural elements acting in opposite directions.

FIG. 5 shows the catheter 2, in which are integrated two flexural elements 12a, 12b which are essentially identical in design, both therefore having a short and a longer wall side. Depending on which flexural element is filled, the direction of curvature changes since the said two elements exhibit different preferred directions of curvature. If the flexural element 12a is filled, then the catheter tip curves upward, as shown in FIG. 4, and the flexible, non-pressurized flexural element 12b automatically follows the same curvature. Conversely, if the flexural element 12b is filled, the catheter tip curves downward because of the preferred direction of said element, as shown in FIG. 5, and here the non-pressurized flexural element 12a assumes the same change in shape. The respective radius or angle of curvature α that can be achieved depends on the ratio of the material length of the wall sections which are opposite each other and are of different lengths. According to the embodiment and dimensions thereof, the angle of curvature can consequently be varied, as can also, of course, the position of the point of flexure, that is, depending on where the wall section that is "long" in terms of the material used is provided relative to the length of the flexural element.

Figure 6:
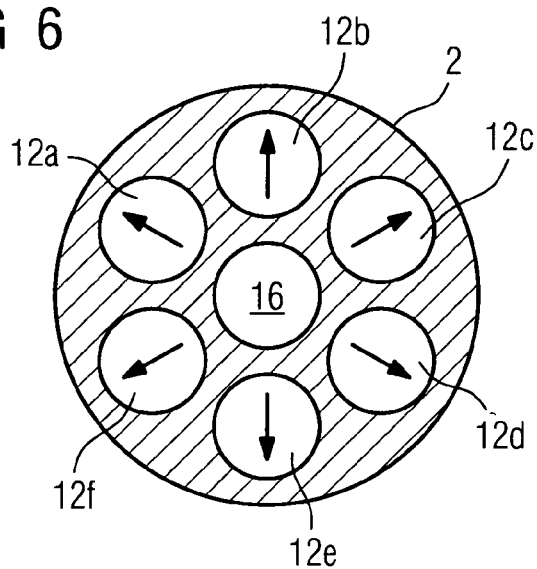
FIG. 6 shows a cross-sectional view through a catheter having a plurality of flexural elements staggered radially outward and disposed in a distributed arrangement.

FIG. 6 shows a cross-sectional view of a catheter 2 around whose central aperture 16, in which, for example, a further working catheter is guided or signal or control lines etc. are routed, six flexural elements 12a, 12b, 12c, 12d, 12e and 12f are arranged, radially staggered outward and, in the example shown, symmetrically distributed. Each of the flexural elements 12a-f can be controlled independently via a separate feed line (not shown in any further detail). The positioning, alignment and design of the flexural elements in the above arrangement is such that each flexural element has its own preferred direction of curvature, said preferred direction of curvature being oriented in a different direction in each case. Said preferred directions of curvature are represented by the respective arrows in the flexural elements. The arrow indicates how the respective flexural element—as shown for example in FIGS. 4 and 5—starts off from the more or less straight catheter shape and then bends in the direction of the arrow. If a plurality of flexural elements are therefore integrated into the catheter and the directions of deformation of the individual flexural elements are aligned as shown in FIG. 6, then a different direction of flexure can be achieved by increasing the pressure in each separate flexural element. Combinations are also possible of course; in other words, pressure can be applied to two adjacent flexural elements such that the resulting direction of flexure is the direction that lies between the individual main element-related directions. It is also conceivable of course for pressure to be applied to all the flexural elements so that the individual effects thereof are cancelled out, but the catheter itself stiffens considerably in the zone where the flexural elements are provided.

Figure 7:
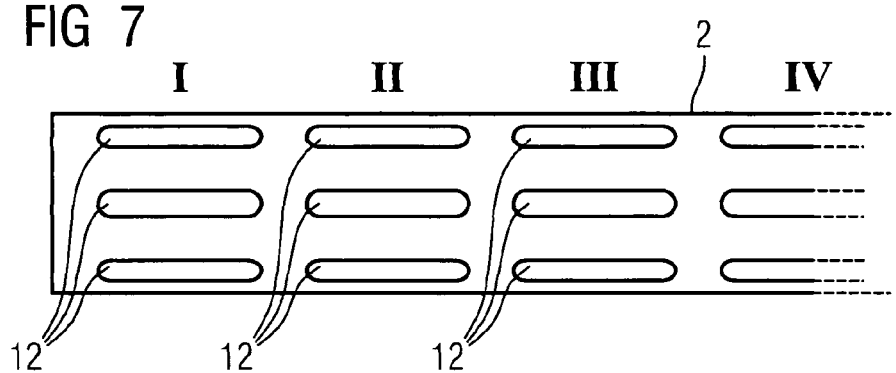
FIG. 7 shows a schematic diagram of a catheter having a plurality of segmentally arranged flexural elements.

With regard to the arrangement of the flexural elements that are staggered radially outward, different embodiments are possible. FIG. 7 shows a catheter 2 in which the flexural elements 12 are disposed in a quasi-segmental arrangement. The figure shows four segments I, II, III, IV in which a plurality of flexural elements 12 are arranged in each case. Based on FIG. 6, six flexural elements distributed in a symmetrical arrangement are contained in each segment (for reasons of presentation only three are shown in FIG. 7). This permits on the one hand a corresponding catheter flexure to be performed segment by segment, and on other hand a segment-by-segment catheter stiffening to be achieved.

Figure 8:
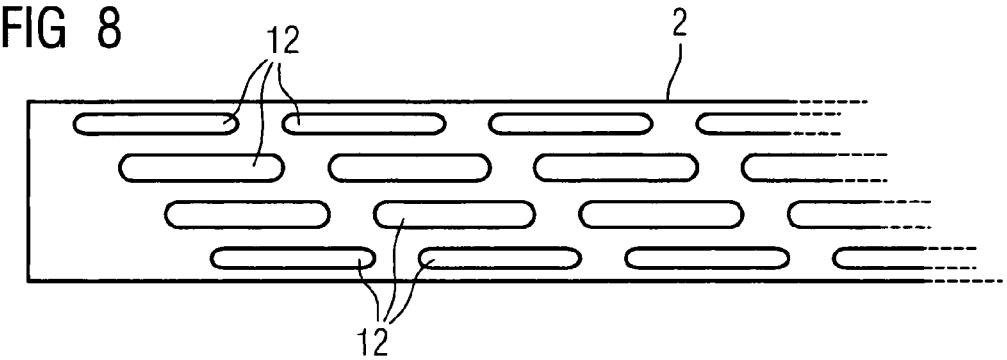
FIG. 8 shows a schematic diagram of a catheter having a plurality of flexural elements disposed in a staggered arrangement over the length of the catheter.

A different type of arrangement of the flexural elements 12 is shown in FIG. 8. In this case, the flexural elements 12 are staggered radially outward as shown in FIG. 6, but they also overlap one another, in other words a kind of spiral-shaped arrangement of the flexural elements is chosen. Since here, too, each flexural element can be activated independently (for the sake of clarity the individual feed lines are not shown in greater detail; the same applies to FIG. 7), a locally defined curvature can also be achieved here.

Figure 9:
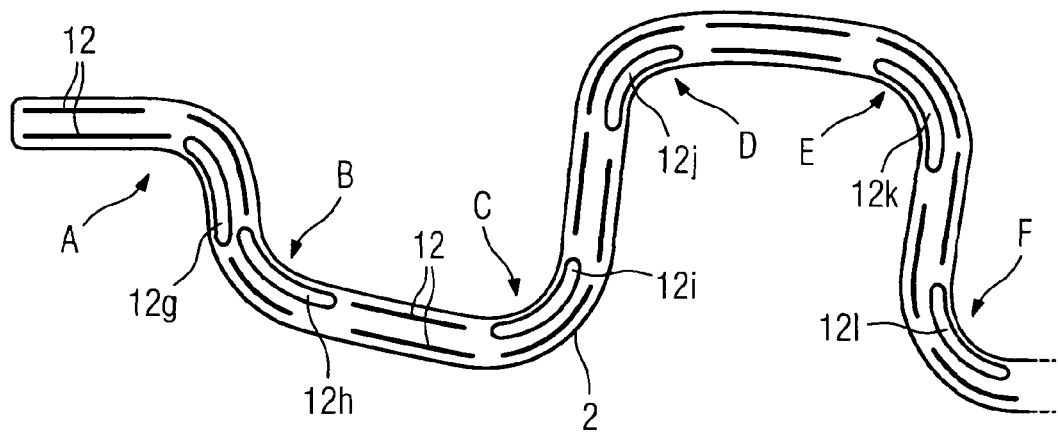
FIG. 9 shows a schematic diagram of a catheter course obtained by activation of different flexural elements.

FIG. 9 is a diagram showing in schematic form an example of the deformation of a catheter 2 that is achievable by separate activation of individual flexural elements. A plurality of individual flexural elements 12 are distributed along the length of part of the catheter. Said elements can either be distributed in segments, as shown in FIG. 7, or staggered in a spiral arrangement, as shown in FIG. 8. A total of six different flexural points A, B, C, D, E and F are shown in FIG. 9. In order to achieve flexure at the flexural point A, the flexural element 12g is activated and the adjacent, in particular opposite flexural elements 12 remain non-pressurized and therefore flexible. In order to achieve flexure at the flexural point B, the flexural element 12h is activated, and in order to achieve flexure at the flexural point C, the flexural element 12i is activated. A similar procedure is followed in order to achieve flexure at the flexural point D, and here the flexural element 12j is activated by the feed device. In order to achieve flexure at the flexural point E, the flexural element 12k is activated, and finally in order to achieve flexure at the flexural point F, the flexural element 12l is activated. As the diagram shows, the fact that each of said flexural elements has a defined preferred direction of curvature and assumes said curvature when in a pressurized state results in the whole of the catheter in the respective area assuming the corresponding curvature and consequently producing the highly convoluted shape shown in FIG. 9.

The flexural elements can be of any length and to allow sufficient flexure relative to the diameter of the catheter, they should be at least 1 cm or more in length. The diameter thereof varies according to the type and diameter of the catheter and the type of arrangement of the flexural elements and the number thereof. It should be at least 1 mm or more in length.

Figure 10:
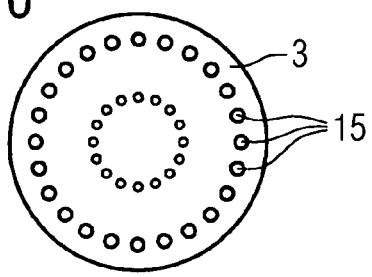
FIG. 10 shows a schematic diagram of a connection device of the catheter.

Finally, FIG. 10 shows a schematic representation of the connection device 3 of the catheter 2. As can be seen, a plurality of feed lines 15, each of which leads to a specific flexural element 12, converge in the connection device 3. Different codings or suchlike are provided at the connection device 3 to indicate which feed line 15 leads to which flexural element. This can take the form, for example, of a plug-in coding, that is to say the two connection devices 3 and 4 can only be coupled to each other in a quite specific manner, so that the respective feed line 15 is then identified on the basis of a defined positional assignment. Alternatively it is also conceivable that other information means such as transponders or the like permit the identification.

All in all, the catheter or, as the case may be, the catheter device according to the invention permits easy navigation, since the physician can perform a desired catheter flexure or tip deformation as required based on the anatomical conditions in the blood vessel under investigation. By this means it is also possible, when a plurality of segments are activated, to achieve a specific catheter shape and "freeze" it, in other words the catheter can be, as it were, "braced out" in the blood vessel. If the catheter is a guidance catheter in which a working catheter is guided for example for a biopsy or suchlike, no dislocation of the catheter can occur on account of the "bracing out" if, for example, a wall or suchlike has to be penetrated by means of the working catheter or if the catheter runs up against such a wall.

The invention claimed is:

1. A catheter for inserting into a hollow organ, comprising a plurality of flexural elements, wherein the flexural elements are:
   arranged inside the catheter;
   flexible in a non-pressurized state;
   adapted to stiffen upon an internal pressure applied to the flexural element by the filling medium; and
   adapted to an assumed predetermined curved shape as a result of the applied internal pressure to provide a flexibility of the catheter and reduce a risk of patient injury when the catheter is advanced in the hollow organ,
   wherein the plurality of flexural elements each of which are adapted to be selectively filled with the filling medium, and
   wherein the flexural elements are arranged over a length of the catheter in segments one after the other at the center of the catheter relative to a longitudinal axis of the catheter to achieve a flexural curve of the catheter at a plurality of different longitudinal locations by activating the flexural elements of one of the segments,
   wherein each of the flexural elements is shaped as a tube that is made of a non-elastic plastic material and has a shorter wall length on one side and a longer wall length on an opposite side before filling with the filling medium and the curved shape is obtained as a result of different wall lengths of the each of the flexural elements after filling with the filling medium.

2. The catheter according to claim 1, wherein the hollow organ is a blood vessel.

3. The catheter according to claim 1, wherein the internal pressure of each flexural element is separately controllable using the filling medium.

4. The catheter according to claim 1, wherein the flexural elements are constructed and arranged such that each flexural element has, upon appliance of the internal pressure, a predetermined deformation direction different from the predetermined deformation directions of the other flexural elements.

5. The catheter according to claim 1, wherein each of the segments locates at a common longitudinal position of the catheter along the longitudinal axis of the catheter and comprises at least two of the flexural elements.

6. The catheter according to claim 1, wherein each of the segments does not locate at a common longitudinal position of the catheter along the longitudinal axis of the catheter, and wherein the segments are overlapped with each other along the longitudinal axis of the catheter and each of the segments comprises at least two of the flexural elements.

7. The catheter according to claim 1, wherein the material is polyurethane or polytetrafluoroethylene.

8. The catheter according to claim 1, wherein the filling medium is a liquid or a gas.

9. The catheter according to claim 8, wherein the filling medium is a liquid chosen from the group consisting of water, a saline solution and a biocompatible fluid.

10. The catheter according to claim 8, wherein the filling medium is a gas chosen from the group consisting of air, oxygen and a biocompatible gas.

11. The catheter according to claim 1, further comprising a central connecting device connected to a supply device for feeding the filling medium to the flexural elements via a plurality of feeding lines, the feeding lines separately connected to the flexural elements and commonly to the central connecting device.

12. A catheter device, comprising:
   a catheter for inserting into a hollow organ, comprising a plurality of flexural elements, wherein the flexural elements are:
   arranged inside the catheter;
   flexible in a non-pressurized state;
   adapted to stiffen upon an internal pressure applied to the flexural element by the filling medium; and
   adapted to an assumed predetermined curved shape as a result of the applied internal pressure to provide a flexibility of the catheter and reduce a risk of patient injury when the catheter is advanced in the hollow organ; and
   a supply device connected to the catheter for feeding the filling medium to the flexural element,
   wherein the flexural elements each of which are adapted to be selectively filled with the filling medium, and
   wherein the flexural elements are arranged over a length of the catheter in segments one after the other at the center of the catheter relative to a longitudinal axis of the catheter to achieve a flexural curve of the catheter at a plurality of different longitudinal locations by activating the flexural elements of one of the segments,
wherein each of the flexural elements is shaped as a tube that is made of a non-elastic plastic material and has a shorter wall length on one side and a longer wall length on an opposite side before filling with the filling medium and the curved shape is obtained as a result of different wall lengths of the each of the flexural elements after filling with the filling medium.

13. The catheter device according to claim 12, wherein the catheter comprises a plurality of flexural elements and the supply device is adapted to activate the flexural elements individually by feeding the filling medium to the flexural elements so that at least two flexural elements have a different internal pressure when fed with the filling medium.

14. The catheter device according to claim 13, further comprising:
a central connecting device connected to the supply device for feeding the filling medium to the flexural elements via a plurality of feeding lines, the feeding lines separately connected to the flexural elements and commonly to the central connecting device; and
an evaluation device for identifying the feeding lines commonly connected to the connecting device.

15. The catheter device according to claim 12, wherein the supply device is controlled by a control device using input data comprising a desired curvature of the flexural element, the control device activating the supply device to feed the filling medium to the flexural element such that the desired curvature of the flexural element is obtained.

16. The catheter device according to claim 15, further comprising an input device connected to the control device for inputting the input data.

17. The catheter device according to claim 16, wherein the input device includes a monitor for displaying an image of the hollow organ and the inserted catheter and the input device includes a marking set by a user on the monitor.

18. The catheter according to claim 6, wherein the flexural elements are spirally arranged along the longitudinal axis of the catheter.

* * * * *